(12) United States Patent
Schwindeman et al.

(10) Patent No.: US 6,717,014 B1
(45) Date of Patent: Apr. 6, 2004

(54) PROCESSES FOR PREPARING HALOAMINES AND TERTIARY AMINOALKYLORGANOMETALLIC COMPOUNDS

(75) Inventors: James Anthony Schwindeman, Lincolnton, NC (US); Randy W. Hall, Kings Mountain, NC (US); Sonia S. Stryker, Charlotte, NC (US)

(73) Assignee: FMC Corporation, Philadelphia, PA (US)

( * ) Notice: Subject to any disclaimer, the term of this patent is extended or adjusted under 35 U.S.C. 154(b) by 1002 days.

(21) Appl. No.: 08/882,513

(22) Filed: Jun. 25, 1997

Related U.S. Application Data

(60) Provisional application No. 60/022,225, filed on Jul. 19, 1996, and provisional application No. 60/020,781, filed on Jun. 28, 1996.

(51) Int. Cl.[7] ............... C07D 243/00; C07D 243/08; C07D 405/00; C07C 211/00
(52) U.S. Cl. ............ 564/310; 540/553; 540/575; 540/596; 564/310
(58) Field of Search ............... 540/553, 575; 540/596; 564/310

(56) References Cited

U.S. PATENT DOCUMENTS

| | | | | |
|---|---|---|---|---|
| 4,616,069 A | * | 10/1986 | Watanabe et al. | 525/370 |
| 5,496,940 A | | 3/1996 | Lawson et al. | 540/450 |
| 5,523,364 A | * | 6/1996 | Engel et al. | 526/180 |
| 5,527,753 A | | 6/1996 | Engel et al. | 502/155 |

FOREIGN PATENT DOCUMENTS

| CZ | 248547 | 7/1988 |
|---|---|---|

OTHER PUBLICATIONS

K. Ueda et al., "Synthesis of Polymers with Amino End Groups. 3. Reactions of Anionic Living Polymers with α–Halo–ω–aminoalkanes With A Protected Amino Functionality", *Macromolecules*, vol. 23, No. 4, pp. 939–945, 1990.

A. Hirao et al., "Synthesis of Polymers with Carboxy End Groups by Reaction of Polystyryl Anions with 4–Bromo–1,1,1–trimethoxybutane", *Macromolecules*, vol. 26, No. 9, pp. 2145–2150, Apr., 1993.

F.F. Huerta et al., "DTBB–Catalysed Lithiation of 4–Functionalised 1–Chloro–2–Butenes", *Tetrahedron*, vol. 52, No. 41, pp. 13243–13254, 1996.

N.J. Leonard et al., "Small Charged Rings. XI.[1] Synthesis and Reactions of 1,1,2,2–Tetrasubstituted Azetidinium Salts[2]", *Journal of Organic Chemistry*, vol. 33, No. 4, pp. 1322–1333, Apr., 1968.

M.J. Stewart et al., "Anionic Functional Initiators. 1: 3–Dimethylaminopropyllithium as an Initiator for the Synthesis of Bi– and Difunctional Polybutadienes", *British Polymer Journal*, vol. 22, No. 4, pp.319–325, 1990.

* cited by examiner

*Primary Examiner*—Sabiha Qazi
(74) *Attorney, Agent, or Firm*—Myers Bigel Sibley & Sajovec, PA

(57) ABSTRACT

Processes for the preparation of haloalkylamines and tertiary aminoalkylorganometallic compounds are disclosed. The haloalkylamines can be prepared by direct reaction of an amine with an α,ω-dihaloalkane or an α,ω-dihaloalkene. Tertiary aminoalkylorganometallic compounds can be prepared by reacting selected tertiary haloalkylamines with an alkali metal at a temperature greater than 45° C. in hydrocarbon solvents.

19 Claims, No Drawings

PROCESSES FOR PREPARING HALOAMINES AND TERTIARY AMINOALKYLORGANOMETALLIC COMPOUNDS

CROSS REFERENCE TO RELATED APPLICATION

This application is related to commonly owned Provisional Application Ser. No. 60/020,781, filed Jun. 28, 1996 and Provisional Application Ser. No. 60/022,225, filed Jul. 19, 1996, and claims the benefit of the earlier filing date under 35 U.S.C. 119(e).

FIELD OF THE INVENTION

This invention is directed to processes for preparing haloamines and aminoalkylorganometallic compounds.

BACKGROUND OF THE INVENTION

Haloamines of the general formula $R^1R^2N-(CH_2)_n-X$ (wherein X is halide) can be used for a variety of organic synthesis applications, such as precursors for functionalized amine initiators (U.S. Pat. No. 5,496,940) or as electrophiles for functionalization of polymers (Ueda, Hirao, and Nakahama, *Macromolecules*, 23, 939–945 (1990)).

Some common literature synthetic methods for the preparation of haloamines involve the chlorination of an omega-amino alcohol with thionylchloride (Leonard and Durand, *J. Org. Chem.*, 33, 1330 (1968), as represented below by Equation 1:

Equation 1:

$$R^1R^2N-(CH_2)_n-OH+SOCl_2 \rightarrow R^1R^2N-(CH_2)_n-Cl$$

Haloamines can also be prepared by the reaction of an omega-haloalcohol with an amine, as reported in Czech Patent CS 248547 B1 880701, represented below by Equation 2:

Equation 2:

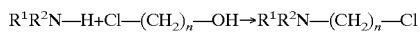

$$R^1R^2N-H+Cl-(CH_2)_n-OH \rightarrow R^1R^2N-(CH_2)_n-Cl$$

These methods, however, can require very expensive raw materials and are typically inconvenient, due to the lack of availability of these raw materials, the omega-amino- and halo-alcohols.

U.S. Pat. No. 5,496,940 reports another method for preparing haloamines by the reaction of a lithium amide with the alkylhalide to form the haloamine, represented by Equation 3 below.

Equation 3:

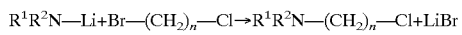

$$R^1R^2N-Li+Br-(CH_2)_n-Cl \rightarrow R^1R^2N-(CH_2)_n-Cl+LiBr$$

This method, however, is also expensive. Further, there can be safety concerns associated with this method due to the employment of lithium-based reagents.

Haloamines such as those prepared as described above are useful for a variety of organic synthesis applications. For example, U.S. Pat. No. 5,496,940 reports a process for the preparation of aminoalkyllithium compounds by reacting a haloamine with two or more equivalents of an alkyllithium reagent, such as tert-butyllithium, in a solvent preferably at a temperature less than 38° C. An exemplary reaction is set forth below by Equation 4:

Equation 4:

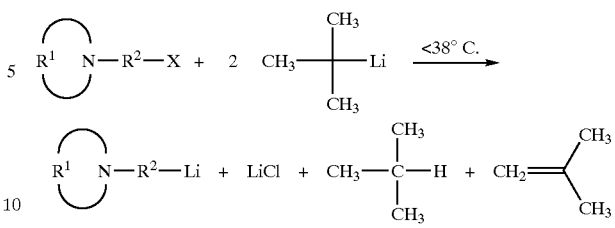

Monofunctional anionic initiators possessing amine functionalities are useful in preparing amino-terminated styrene-butadiene rubbers (SBRs). See European Patent Application 593049A1 and U.S. Pat. No. 5,496,940. These elastomers have been shown to possess increased rebound, decreased rolling resistance, and lower heat build-up (reduced hysteresis). They are useful in forming improved, energy efficient tires, power belts, and mechanical goods.

SUMMARY OF THE INVENTION

The present invention provides processes for preparing haloamines, which can avoid the economic and safety issues associated with prior procedures. In this aspect of the invention, haloamines are prepared by reacting an amine directly with an α,ω-dihaloalkane or an α,ω-dihaloalkene, optionally in the presence of an inorganic or organic acid acceptor, and optionally in a solvent. These haloamines can be prepared from inexpensive, readily available raw materials, namely, α,ω-dihaloalkanes and α,ω-dihaloalkenes and the corresponding amine.

The present invention also provides processes for the synthesis of aminoalkylorganometallic compounds. In this aspect of the invention, alkali metal, such as lithium, is reacted with a suitable haloamine, exclusively, in a hydrocarbon solvent to produce alkylalkali metal compounds containing tertiary amines. Because alkali metal, and not alkylorganometallic compounds, is used in the metallation of the haloamine, the processes of the invention can offer cost savings and safety improvements. In addition, unexpectedly, consistently higher yields can be obtained when the halogen-metal exchange reaction is conducted at elevated temperatures (>45° C.). Less unreacted starting material can also be present when the halogen-metal exchange is conducted at elevated temperatures. Still further, the Wurtz coupling by-product, for example, as illustrated by Equation 5, can be minimized when the halogen-metal exchange is conducted at elevated temperatures.

Equation 5:

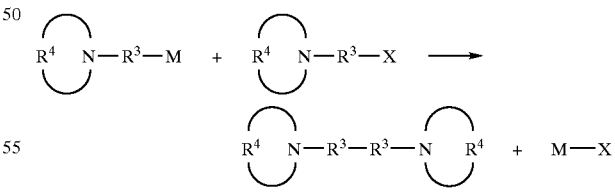

In addition, initiation of the metal-halogen exchange can be very consistent at the elevated temperatures. This consistent initiation can increase the safety of this process, in contrast to the methods detailed in the prior art.

DETAILED DESCRIPTION OF THE INVENTION

In one aspect of the invention, haloamines of the formula $R^1R^2N-R^3X^2$ (I) (singly and mixtures) can be prepared, wherein:

R$^1$ and R$^2$ are independently chiral or achiral and independently selected from the group consisting of hydrogen; saturated or unsaturated, linear or branched, C1 to C16 alkyl; saturated or unsaturated C3–C16 cycloalkyl; saturated or unsaturated, linear or branched, silyl-, amino- or oxy-substituted C1–C16 alkyl; saturated or unsaturated silyl-, amino- or oxy-substituted C3–C16 cycloalkyl; saturated or unsaturated, linear or branched, substituted C1–C16 alkyl containing saturated or unsaturated linear or branched C1 to C8 lower alkyl, C3–C16 cycloalkyl, C3–C10 aryl, or substituted aryl containing saturated or unsaturated linear or branched C1–C8 lower alkyl or C3–C8 cycloalkyl; saturated or unsaturated substituted C3–C16 cycloalkyl containing saturated or unsaturated linear or branched C1–C8 lower alkyl, C3–C8 cycloalkyl, C3–C10 aryl, or substituted aryl containing saturated or unsaturated linear or branched C1–C8 lower alkyl or C3–C8 cycloalkyl; or R$^1$ and R$^2$ together may represent a C4–C16 alkylene R$^4$

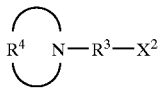

which alkylene may be saturated or unsaturated, optionally substituted with silyl, amino, or oxygen, or optionally substituted with saturated or unsaturated linear or branched C1–C8 alkyl, C3–C8 cycloalkyl, C3–C10 aryl, or substituted aryl containing saturated or unsaturated linear or branched C1–C8 lower alkyl or C3–C8 cycloalkyl;

R$^3$ is selected from the group consisting of saturated or unsaturated, linear or branched, C3–C25 alkyl; saturated or unsaturated C3–C25 cycloalkyl; saturated or unsaturated, linear or branched, substituted C3–C25 alkyl containing saturated or unsaturated linear or branched C1–C8 alkyl, C3–C8 cycloalkyl, C3–C10 aryl, or substituted aryl containing saturated or unsaturated linear or branched C1–C8 alkyl or C3–C8 cycloalkyl; saturated or unsaturated substituted C3–C25 cycloalkyl containing saturated or unsaturated linear or branched C1–C8 alkyl, C3–C8 cycloalkyl, C3–C10 aryl, or substituted aryl containing saturated or unsaturated linear or branched C1–C8 alkyl or C3–C8 cycloalkyl; and X$^2$ is halogen, such as chlorine and bromine.

Haloamines of Formula I can be prepared as illustrated below:

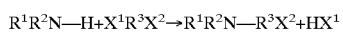

wherein R$^1$, R$^2$, R$^3$ and X$^2$ are the same as defined above, and X$^1$ is also halogen which may be the same or different as X$^2$.

Exemplary α,ω-dihaloalkanes and α,ω-dihaloalkenes include, but are not limited to, 1-bromo-3-chloro-propane, 1-bromo-4-chloro-butane, 1-bromo-5-chloro-pentane, 1-bromo-6-chloro-hexane, 1-bromo-8-chloro-octane, 1,4-dichloro-2-butene, 1,3-dibromopropane, 1,3-dichloropropane, 1,4-dibromobutane, 1,4-dichlorobutane, 1-bromo-3-chloro-2-methylpropane, 1,3-dibromo-2-methylpropane, 1,3-dichloro-2-methylpropane, 1,3-dichloro-2,2-dimethylpropane, 1,3-dibromo-2,2-dimethylpropane, 1-bromo-3-chloro-2,2-methylpropane, and the like, and mixtures thereof.

Examples of suitable amines useful in this invention include, but are not limited to, t-butyl amine, hexamethyleneimine, 1-methyl-1,4-diaza-cycloheptane (1-methylhomopiperazine), piperidine, pyrrolidine, ethyl amine, dimethyl amine, morpholine, 1-methyl piperazine, and the like, and mixtures thereof.

An inorganic or organic acid acceptor may be optionally employed in the synthesis described above. Examples of suitable acid acceptors include, but are not limited to, potassium carbonate, sodium bicarbonate, triethylamine, pyridine, trimethylamine, and the like, and mixtures thereof.

Solvents (hydrocarbon and polar solvents) may be optionally employed in the synthesis of haloamines in accordance with the present invention. Suitable solvents include, but are not limited to, water, tetrahydrofuran, hexane, cyclohexane, toluene, acetonitrile, methyl-t-butyl ether, diethoxymethane, methanol, and the like and mixtures thereof.

In another aspect of the invention, processes for preparing tertiary aminoalkylorganometallic compounds are provided. Tertiary aminoalkylorganometallic compounds prepared in accordance with the present invention are represented generally by the formula R$^1$R$^2$N—R$^3$—M (II) (singly and mixtures thereof), wherein:

R$^1$ and R$^2$ are independently chiral or achiral and independently selected from the group consisting of hydrogen; saturated or unsaturated, linear or branched, C1 to C16 alkyl; saturated or unsaturated C3–C16 cycloalkyl; saturated or unsaturated, linear or branched, silyl-, amino- or oxy-substituted C1–C16 alkyl; saturated or unsaturated silyl-, amino- or oxy-substituted C3–C16 cycloalkyl; saturated or unsaturated, linear or branched, substituted C1–C16 alkyl containing saturated or unsaturated linear or branched C1 to C8 lower alkyl, C3–C16 cycloalkyl, C3–C10 aryl, or substituted aryl containing saturated or unsaturated linear or branched C1–C8 lower alkyl or C3–C8 cycloalkyl; saturated or unsaturated substituted C3–C16 cycloalkyl containing saturated or unsaturated linear or branched C1–C8 lower alkyl, C3–C8 cycloalkyl, C3–C10 aryl, or substituted aryl containing saturated or unsaturated linear or branched C1–C8 lower alkyl or C3–C8 cycloalkyl; or R$^1$ and R$^2$ together may represent a C4–C16 alkylene R$^4$

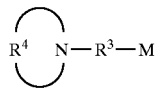

which alkylene may be saturated or unsaturated, optionally substituted with silyl, amino, or oxygen, or optionally substituted with saturated or unsaturated linear or branched C1–C8 alkyl, C3–C8 cycloalkyl, C3–C10 aryl, or substituted aryl containing saturated or unsaturated linear or branched C1–C8 lower alkyl or C3–C8 cycloalkyl;

R$^3$ is selected from the group consisting of saturated or unsaturated, linear or branched, C3–C25 alkyl; saturated or unsaturated C3–C25 cycloalkyl; saturated or unsaturated, linear or branched, substituted C3–C25 alkyl containing saturated or unsaturated linear or branched C1–C8 alkyl, C3–C8 cycloalkyl, C3–C10 aryl, or substituted aryl containing saturated or unsaturated linear or branched C1–C8 alkyl or C3–C8 cycloalkyl; saturated or unsaturated substituted C3–C25 cycloalkyl containing saturated or unsaturated linear or branched C1–C8 alkyl, C3–C8 cycloalkyl, C3–C10 aryl, or substituted aryl containing saturated or unsaturated linear or branched C1–C8 alkyl or C3–C8 cycloalkyl; and M is an alkali metal, preferably lithium, and mixtures thereof.

The improved processes of the invention for preparing aminoalkylorganometallic compounds involves the reaction of selected tertiary haloalkylamines, such as described above of Formula I, singly and mixtures thereof, wherein the $R^3$ group is a connecting or tether group which contains three to twenty-five carbon atoms, with an alkali metal selected from lithium, sodium and potassium, and mixtures thereof, at an elevated temperature (>45° C.), in a hydrocarbon solvent containing five to ten carbon atoms and mixtures of such solvents to form alkylorganometallic compounds (singly and mixtures thereof) containing an amine, such as represented by Formula II above.

Examples of haloamines useful in the practice of this aspect of the invention include, but are not limited to, 3-(N,N-dimethylamino)-1-propyl halide, 3-(N,N-dimethylamino)-2-methyl-1-propyl halide, 3-(N,N-diethylamino)-2,2-dimethyl-1-propyl halide, 5-(N,N-dimethylamino)-1-pentyl halide, 4-(N-ethyl-N-methylamino)-1-butyl halide, 3-(piperidino)-1-propyl halide, 3-(pyrrolidino)-2-methyl-1-propyl halide, 6-(pyrrolidino)-1-hexyl halide, 3-(hexamethyleneimino)-1-propyl halide, 3-(hexamethyleneimino)-2,2-dimethyl-1-propyl halide, 4-(hexamethyleneimino)-2-butenyl-1-halide, 3-(1,4-diaza-4-methyl-1-cycloheptyl)-1-propyl halide, 4-(1,4-diaza-4-methyl-1-cycloheptyl)-1-butyl halide, 3-(N-isopropyl-N-methyl)-2-methyl-1-propyl halide, 3-(2,2,5,5-tetramethyl-2,5-disila-1-azacyclopentane)-1-propyl halide, 4-(2,2,5,5-tetramethyl-2,5-disila-1-azacyclopentane)-1-butyl halide, 6-(2,2,5,5-tetramethyl-2,5-disila-1-azacyclopentane)-1-hexyl halide, and the like, and mixtures thereof.

Examples of hydrocarbon solvents include, but are not limited to, cyclohexane, pentane, hexane, heptane, octane, cyclopentane, methylcyclohexane, toluene, ethylbenzene, cumene, and the like, and mixtures thereof.

The alkali metal used in preparing the aminoalkylorganometallic compounds containing amines of Formula II is selected from lithium, sodium and potassium, and preferably is used as a dispersion whose particle size usually does not exceed about 300 microns. Preferably the particle size is between 10 and 300 microns, although coarser particle size alkali metal can be used. When lithium is used, the lithium metal can contain 0.2 to 1.0, and preferably 0.8, weight percent sodium. The alkali metal is used in amounts of 90% of theoretical to a 400% excess above the theoretical amount necessary to produce the compounds of Formula II. The reaction temperature is greater than about 45° C. up to just below the decomposition of the reactants and/or the product. An abrasive as known in the art can be optionally added to improve the metallation reaction. The yields of tertiary aminoalkylorganometallic compounds prepared by this invention typically exceed 90%.

Advantages of the elevated temperature process to prepare the tertiary aminoalkylorganometallic compounds include: higher yield of desired product; less Wurtz coupling by-product; less unreacted haloamino starting material; more consistent initiation; and less soluble lithium chloride by-product.

For example, the isolated yield of 3-(hexamethyleneimino)-1-propyllithium was 94.9% when it was prepared at elevated temperature (55–65° C.). When the same aminoalkyllithium compound was prepared at 33–39° C., the yield plummeted to 77.8%.

This aspect of the invention is illustrated, for example, by Equation 6:

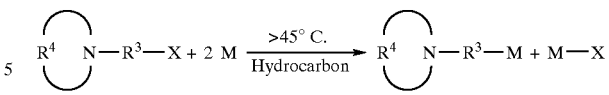

The tertiary aminoalkylorganometallic compounds can have utility as initiators in anionic polymerization of conjugated dienes and alkenylsubstituted aromatic compounds. The resultant polymer, which contains a tertiary amino group, can exhibit improved characteristics, such as improved hysteresis loss characteristics.

The following examples further illustrate the invention.

SYNTHESIS OF HALOAMINES

EXAMPLE 1

Preparation of 1-(3-Chloropropyl)-hexamethyleneimine

A round-bottom, 250 milliliter, three-necked flask was equipped with a mechanical stirrer, a Claisen adapter, equipped with a thermocouple and a dry-ice condenser with a gas inlet, and a pressure-equalizing dropping funnel. This apparatus was baked in an oven overnight at 125° C., assembled hot, and purged with argon until cool. The reaction flask was charged with 1-bromo-3-chloropropane 15.74 grams, (0.1 moles, 1 equivalent). The reaction mixture was stirred at 300 RPM's. Hexamethyleneimine 19.84 grams, (0.2 moles, 2 equivalents) was added dropwise via the addition funnel over a period of one hour. A hexane/dry ice cooling bath was applied as needed to maintain a reaction temperature no greater than 35° C. After addition was complete, samples of the reaction mixture were removed periodically, washed with saturated sodium bicarbonate solution, and assayed for unreacted 1-bromo-3-chloropropane by gas chromatography (GLC). The reaction was allowed to stir overnight. Next, 50 milliliters of cyclohexane was added to the reaction flask and allowed to stir overnight. Then, 75 milliliters of saturated sodium bicarbonate solution was added to the reaction flask and allowed to stir overnight. The reaction mixture was then transferred to a 500 milliliter separatory funnel where the aqueous layer was drawn off. The reaction mixture was then washed with 75 milliliters of saturated sodium bicarbonate solution. Next, the organic layer was washed with 3×75 milliliters of distilled water and subsequently with 2×75 milliliters of saturated sodium chloride solution. The resulting organic layer was then dried with sodium sulfate, filtered, and concentrated on a rotary evaporator, to afford a clear solution with a yield=10.82 grams; 61.6% (GC assay=98.08%).

EXAMPLE 2

Preparation of 1-(3-Chloropropyl)-hexamethyleneimine

A round-bottom, one liter, four-necked flask was equipped with a mechanical stirrer, a sample port, a Claisen adapter, equipped with a thermocouple and a dry-ice condenser with a gas inlet, and a pressure-equalizing dropping funnel. This apparatus was baked in an oven overnight at 125° C., assembled hot, and purged with argon until cool. The reaction flask was charged with 1-bromo-3-chloropropane 157.42 grams, (1.0 moles, 1 equivalent), potassium carbonate 276.38 grams (2.0 moles, 2 equivalents), cyclohexane 42.63 grams, (0.50 moles, 0.5 equivalents), and methyl-t- butyl ether 44.26 grams, (0.50 moles, 0.5 equivalents). The reaction mixture was stirred at 300 RPM's. Hexamethyleneimine 99.18 grams, (1.0 moles, 1 equivalent) was added dropwise via the addition funnel over a period of eighty-three minutes. A hexane/dry ice cooling bath was applied as needed to maintain a reaction temperature no greater than 35° C. After addition was complete, samples of the reaction mixture were removed periodically, washed with saturated sodium bicarbonate solution, and assayed for unreacted 1-bromo-3-chloropropane by gas chromatography (GLC). The reaction was allowed to stir overnight. Next, 200 milliliters of cyclohexane was added to the reaction flask and allowed to stir overnight. Then, 200 milliliters of saturated sodium bicarbonate solution was added to the reaction flask and allowed to stir overnight. The reaction mixture was then transferred to a two liter separatory funnel where the aqueous layer was drawn off. The reaction mixture was then washed with 200 milliliters of saturated sodium bicarbonate solution. Next, the organic layer was washed with 3×200 milliliters of distilled water and subsequently with 2×200 milliliters of saturated sodium chloride solution. The resulting organic layer was then dried with sodium sulfate, filtered, and concentrated on a rotary evaporator, to afford a clear solution with a yield=154.05 grams; 87.8% (GC assay=93.3%).

EXAMPLE 3

Preparation of 1-(3-Chloropropyl)-hexamethyleneimine

A Morton cleaved, five liter, three-necked flask was equipped with a mechanical stirrer, a Claisen adapter, equipped with a thermocouple and a dry-ice condenser with a gas inlet, and a pressure-equalizing dropping funnel. This apparatus was baked in an oven overnight at 125° C., assembled hot, and purged with argon until cool. The reaction flask was charged with 1-bromo-3-chloropropane 786.56 grams, (5.00 moles, 1 equivalent) and cyclohexane 480.02 grams, (5.7 moles, 1.14 equivalents). The reaction mixture was stirred at 200 RPM's. Hexamethyleneimine 990.99 grams, (10.00 moles, 2 equivalents) was added dropwise via the addition funnel over a period of four hours and forty minutes. A hexane/dry ice cooling bath was applied as needed to maintain a reaction temperature no greater than 35° C. After addition was complete, samples of the reaction mixture were removed periodically, washed with saturated sodium bicarbonate solution, and assayed for unreacted 1-bromo-3-chloropropane by gas chromatography (GLC). The reaction was allowed to stir until 1-bromo-3-chloro-propane was consumed. Next, 750 milliliters of cyclohexane was added to the reaction flask and allowed to stir thirty minutes. Then, 1.5 liters of saturated sodium bicarbonate solution was added to the reaction flask and allowed to stir one hour. The reaction mixture was then transferred to a four liter separatory funnel where the aqueous layer was drawn off. The resulting organic layer was then dried with sodium hydroxide pellets to afford a slightly hazy solution with a yield=1814.37 grams of 40.7 wt. % solution; 83% (GC assay=95.8%).

EXAMPLE 4

Preparation of 1-(3-Chloropropyl)-4-methylhomopiperizine

A round-bottom, 250 milliliter, three-necked flask was equipped with a mechanical stirrer, a Claisen adapter, equipped with a thermocouple and a dry-ice condenser with a gas inlet, and a pressure-equalizing dropping funnel. This apparatus was baked in an oven overnight at 125° C., assembled hot, and purged with argon until cool. The reaction flask was charged with 1-bromo-3-chloropropane 15.75 grams, (0.10 moles, 1 equivalent) and cyclohexane 8.68 grams, (0.10 moles, 1 equivalent). The reaction mixture was stirred with a magnetic stir bar. 1-Methylhomopiperizine 22.64 grams, (0.20 moles, 2 equivalents) was added dropwise via the addition funnel over a period of thirty-three minutes. A hexane/dry ice cooling bath was applied as needed to maintain a reaction temperature no greater than 35° C. After addition was complete, samples of the reaction mixture were removed periodically, washed with saturated sodium bicarbonate solution, and assayed for unreacted 1-bromo-3-chloropropane by gas chromatography (GLC). The reaction was allowed to stir until 1-bromo-3-chloro-propane was consumed. Next, 75 milliliters of saturated sodium bicarbonate solution and 25 milliliters of distilled water were added to the reaction flask. The reaction mixture was then transferred to a separatory funnel (homogeneous mixture). The mixture was extracted 2×75 milliliters with ethyl ether. The resulting organic layer was then dried with magnesium sulfate, filtered, and concentrated on a rotary evaporator, to afford a slightly hazy solution with a yield=42%; (GC assay=98.3%).

EXAMPLE 5

Preparation of 1-(4-Chloro-2-butenyl)-hexamethyleneimine

A round-bottom, 250 milliliter, three-necked flask is equipped with a mechanical stirrer, a Claisen adapter, equipped with a thermocouple and a dry-ice condenser with a gas inlet, and a pressure-equalizing dropping funnel. This apparatus is baked in an oven overnight at 125° C., assembled hot, and purged with argon until cool. The reaction flask is charged with 1,4-dichloro-2-butene, 12.50 grams (0.1 moles, 1 equivalent). The reaction mixture is stirred at 300 RPM's. Hexamethyleneimine, 19.84 grams (0.2 moles, 2 equivalents) is added dropwise via the addition funnel over a period of one hour. A hexane/dry ice cooling bath is applied as needed to maintain a reaction temperature no greater than 35° C. After addition is complete, samples of the reaction mixture are removed periodically, washed with saturated sodium bicarbonate solution, and assayed for unreacted 1,4-dichloro-2-butene by gas chromatography (GLC). Next, 50 milliliters of cyclohexane is added to the reaction flask and allowed to stir overnight. Then, 75 milliliters of saturated sodium bicarbonate solution is added to the reaction flask and allowed to stir 2 hours. The reaction mixture is then transferred to a 500 milliliter separatory funnel where the aqueous layer was drawn off. Next, the organic layer is washed with 3×75 milliliters of distilled water. The resulting organic layer is then dried with sodium sulfate, filtered, and concentrated on a rotary evaporator to afford a clear solution, yield=87.4%; GC assay=97.5%.

EXAMPLE 6

Preparation of N-(3-Chloropropyl)-t-butyl Amine

A round-bottom, 250 milliliter, three-necked flask was equipped with a magnetic stir bar, a Claisen adapter, equipped with a thermocouple and a dry-ice condenser with a gas inlet, and a pressure-equalizing dropping funnel. This apparatus was baked in an oven overnight at 125° C., assembled hot, and purged with argon until cool. The reaction flask was charged with 1-bromo-3-chloropropane 15.74 grams, (0.10 moles, 1 equivalent). t-Butylamine 29.26 grams, (0.40 moles, 4 equivalents) was added dropwise via the addition funnel over a period of one hour. After addition was complete, samples of the reaction mixture were removed periodically, washed with saturated sodium bicarbonate solution, and assayed for unreacted 1-bromo-3-chloropropane by gas chromatography (GLC). The reaction was allowed to stir until 1-bromo-3-chloropropane was consumed. Next, 75 milliliters of saturated sodium bicarbonate solution and 25 milliliters of distilled water were added to the reaction flask. The reaction mixture was then transferred to a separatory funnel and extracted 2×75 milliliters with ethyl ether. The organic layer was then dried with magnesium sulfate, filtered, and concentrated on a rotary evaporator, to afford a colorless, slightly hazy solution with a yield=10.47 g (70%); (GC assay=93%).

SYNTHESIS OF AMINOALKYLLITHIUM COMPOUNDS

EXAMPLE 7

Preparation of 3-(N,N-Dimethylamino)-1-propyllithium

A 500 milliliter, three-necked Morton flask was equipped with a mechanical stirrer, a Claisen adapter equipped with a thermocouple and a dry-ice condenser with a gas inlet, and a 125 milliliter pressure-equalizing dropping funnel. This apparatus was baked in an oven overnight at 125° C., assembled hot, and purged with argon until cool. Lithium dispersion was washed free of mineral oil with hexane (3×100 ml), and pentane (2×100 ml), then dried in a stream of argon. The dry lithium powder, 8.35 grams, (1.20 moles) was transferred to the flask with 250 ml of cyclohexane. This suspension was stirred at 850 RPMs, and heated to 47° C. with a heating mantle. The heat source was removed. A mixture of 1-chloro-3-(N,N-dimethylamino)-propane, 19.64 grams, (0.1615 moles) dissolved in 120 ml of cyclohexane was added dropwise. An exotherm was detected after 13% of the halide feed had been added. A dry ice/hexane cooling bath was applied to maintain the reaction temperature at 45–50° C. The total feed time was thirty-eight minutes. An exotherm was noted until the last drop of feed was added. The dropping funnel was rinsed with 20 ml of cyclohexane. The reaction mixture was stirred at 40–45° C. for fifty minutes, then transferred warm to a sintered glass pressure filter containing 2 grams of filter aid. The filtration was complete in three minutes with three psi argon pressure. The equipment and muds were rinsed with 2×50 ml of warm cyclohexane. This afforded 368.6 grams of a hazy, pale yellow solution. Titration of the active C—Li indicated 0.28 M (0.365 moles/kg) which represented a 83.3% yield.

EXAMPLE 8

Preparation of 3-(Hexamethyleneimino)-1-propyllithium

A 3 liter, three-necked Morton flask was equipped with a mechanical stirrer, a Claisen adapter equipped with a thermocouple and a dry-ice condenser with a gas inlet, and a 500 milliliter pressure-equalizing dropping funnel. This apparatus was baked in an oven overnight at 125° C., assembled hot, and purged with argon until cool. Lithium dispersion was washed free of mineral oil with hexane (3×100 ml), and pentane (2×100 ml), then dried in a stream of argon. The dry lithium powder, 26.81 grams, (3.863 moles) was transferred to the flask with 1700 ml of cyclohexane. Next, 15 ml of 0.33 M 3-(hexamethyleneimino)-1-propyllithium in cyclohexane was added to the reaction mixture. This suspension was stirred at 600 RPMs, and heated to 54.8° C. with a heating mantle. The heat source was removed. 1-Chloro-3-(hexamethyleneimino)propane, 206.29 grams, (1.174 moles) dissolved in 217.1 grams of cyclohexane was added dropwise. An exotherm was detected after 10% of the halide feed had been added. A dry ice/hexane cooling bath was applied to maintain the reaction temperature at 55–65° C. The total feed time was ninety-six minutes. An exotherm was noted until the last drop of feed was added. The reaction mixture was stirred overnight at room temperature. The next day, the reaction mixture was heated to 56° C. then transferred warm to a sintered glass pressure filter containing 15 grams of filter aid while still warm. The filtration was complete in seven minutes with three psi argon pressure. The equipment and muds were rinsed with 2×100 ml of warm cyclohexane. This afforded 1857 grams of a slightly hazy, pale yellow solution. Titration of the active C—Li indicated 0.47 M (0.6003 moles/kg) which represented a 94.9% yield.

EXAMPLE 9

Preparation of 3-(Piperidino)-1-propyllithium

A 2 liter, three-necked Morton flask was equipped with a mechanical stirrer, a Claisen adapter equipped with a thermocouple and a dry-ice condenser with a gas inlet, and a 125 milliliter pressure-equalizing dropping funnel. This apparatus was baked in an oven overnight at 125° C., assembled hot, and purged with argon until cool. Lithium dispersion was washed free of mineral oil with hexane (3×100 ml), and pentane (2×100 ml), then dried in a stream of argon. The dry lithium powder, 11.70 grams, (1.686 moles) was transferred to the flask with 900 ml of cyclohexane. An abrasive, 23.0 grams, was then added. This suspension was stirred at 875 RPMs, and heated to 50° C. with a heating mantle. The heat source was removed. A mixture of 1-chloro-3-(piperidino)-propane, 28.29 grams, (0.175 moles) dissolved in 100 ml of cyclohexane was added dropwise. An exotherm was detected after 36% of the halide feed had been added. A dry ice/hexane cooling bath was applied to maintain the reaction temperature at 45–55° C. The total feed time was thirty minutes. An exotherm was noted until the last drop of feed was added. The reaction mixture was stirred at 45–5° C. for forty minutes, then transferred warm to a sintered glass pressure filter containing 15 grams of filter aid. The filtration was complete in three minutes with three psi argon pressure. The equipment and muds were rinsed with 3×500 ml of warm cyclohexane. This afforded 1948 grams of a hazy, pale yellow solution. Titration of the active C—Li indicated 0.062 M (0.0821 moles/kg) which represented a 91.4% yield.

EXAMPLE 10

Preparation of 3-(N,N-Dimethylamino)-2-methyl-1-propyllithium

A 500 milliliter, three-necked Morton flask was equipped with a mechanical stirrer, a Claisen adapter equipped with a thermocouple and a dry-ice condenser with a gas inlet, and a 125 milliliter pressure-equalizing dropping funnel. This apparatus was baked in an oven overnight at 125° C., assembled hot, and purged with argon until cool. Lithium dispersion was washed free of mineral oil with hexane (3×100 ml), and pentane (2×100 ml), then dried in a stream of argon. The dry lithium powder, 8.20 grams, (1.18 moles)

was transferred to the flask with 250 ml of cyclohexane. An abrasive, 30.7 grams, was then added. This suspension was stirred at 700 RPMs, and heated to 47° C. with a heating mantle. The heat source was removed. A mixture of 1-chloro-3-(N,N-dimethylamino)-2-methyl-propane, 16.86 grams, (0.1243 moles) dissolved in 50 ml of cyclohexane was added dropwise. An exotherm was detected after 9.3% of the halide feed had been added. The total feed time was twenty-nine minutes. An exotherm was noted until the last drop of feed was added. The dropping funnel was rinsed with 20 ml of cyclohexane. The reaction mixture was stirred at 40–45° C. for fifty minutes, then transferred warm to a sintered glass pressure filter containing 2 grams of filter aid. The filtration was complete in thirty minutes with three psi argon pressure. The equipment and muds were rinsed with 2×50 ml of warm cyclohexane. This afforded 361 grams of a hazy, pale yellow solution. Titration of the active C—Li indicated 0.304 moles/kg, which represented a 88.3% yield.

EXAMPLE 11

Preparation of 3-(2,2,5,5-Tetramethyl-2,5-disila-1-azacyclopentane)-1-propyllithium A 500 milliliter, three-necked Morton flask was equipped with a mechanical stirrer, a Claisen adapter equipped with a thermocouple and a dry-ice condenser with a gas inlet, and a 125 milliliter pressure-equalizing dropping funnel. This apparatus was baked in an oven overnight at 125° C., assembled hot, and purged with argon until cool. Lithium dispersion was washed free of mineral oil with hexane (3×100 ml), and pentane (2×100 ml), then dried in a stream of argon. The dry lithium powder, 2.55 grams, (0.367 mole) was transferred to the flask with 175 ml of cyclohexane. This suspension was stirred and heated to reflux (82–83° C.) with a heating mantle. The heat source was removed. 3-(2,2,5,5-Tetramethyl-2,5-disila-1-azacyclopentane)-1-propyl chloride, 28.52 grams, (0.119 moles) was added dropwise. An exotherm was detected after 34% of the halide feed had been added. The halide feed rate was adjusted to maintain reflux. The total feed time was twenty-seven minutes. An exotherm was noted until the last drop of feed was added. The reaction temperature gradually fell off to room temperature. The reaction mixture was stirred at ambient temperature for four hours, then transferred warm to a sintered glass pressure filter containing. The filtration was rapid with three psi argon pressure. The equipment and muds were rinsed with 1×30 ml of warm cyclohexane. This afforded 157.47 grams of a pale yellow solution. Total base=15.2 wt %.; Active C—Li=12.0 wt %.; Yield (based on C—Li)= 76.7%.

EXAMPLE 12

Preparation of 3-(1.4-Diaza-4-methyl-1-cycloheptyl)-1-propyllithium

A 500 milliliter, three-necked Morton flask was equipped with a mechanical stirrer, a Claisen adapter equipped with a thermocouple and a dry-ice condenser with a gas inlet, and a 125 milliliter pressure-equalizing dropping funnel. This apparatus was baked in an oven overnight at 125° C., assembled hot, and purged with argon until cool. Lithium dispersion was washed free of mineral oil with hexane (3×100 ml), and pentane (2×100 ml), then dried in a stream of argon. The dry lithium powder, 8.11 grams, (1.17 moles) was transferred to the flask with 250 ml of cyclohexane. An abrasive, 21.2 grams, was then added. This suspension was stirred at 1000 RPMs, and heated to 60° C. with a heating mantle. The heat source was removed. A mixture of 3-(1,4-diaza-4-methyl-1-cycloheptyl)-1-propyl chloride, 12.61 grams, (0.066 moles) dissolved in 75 ml of cyclohexane was added dropwise. An exotherm was detected after 10.3% of the halide feed had been added. A dry ice/hexane cooling bath was applied to maintain the reaction temperature at 45–50° C. The total feed time was twenty-two minutes. An exotherm was noted until the last drop of feed was added. The dropping funnel was rinsed with 10 ml of cyclohexane. The reaction mixture was stirred at 30–35° C. for two hours, then transferred warm to a sintered glass pressure filter. The filtration was complete in seven minutes with three psi argon pressure. The equipment and muds were rinsed with 2×50 ml of warm cyclohexane. This afforded 315.2 grams of a slightly hazy, orange solution. Titration of the active C—Li indicated 0.092 M (0.1182 moles/kg), which represented a 56.4% yield.

COMPARATIVE EXAMPLE

Preparation of 3-(Hexamethyleneimino)-1-Propyllithium at 35° C.

A 500 milliliter, three-necked Morton flask was equipped with a mechanical stirrer, a Claisen adapter equipped with a thermocouple and a dry-ice condenser with a gas inlet, and a 125 milliliter pressure-equalizing dropping funnel. This apparatus was baked in an oven overnight at 125° C., assembled hot, and purged with argon until cool. Lithium dispersion was washed free of mineral oil with hexane (3×50 ml), and pentane (2×50 ml), then was dried in a stream of argon. The dry lithium powder, 11.46 grams, (1.651 moles) was transferred to the flask with 250 ml of cyclohexane. This suspension was stirred at 800 RPMs, and heated to 35.0° C. with a heating mantle. The heat source was removed. 1-Chloro-3-(hexamethyleneimino)propane, 20.38 grams, (0.1676 moles) dissolved in 100 milliliters of cyclohexane was added dropwise. An exotherm was detected after 11% of the halide feed had been added. A dry ice/hexane cooling bath was applied to maintain the reaction temperature at 33° C.–39° C. The total feed time was fifty-eight minutes. An exotherm was noted until the last drop of feed was added. The reaction mixture was stirred for one hour at room temperature. The reaction mixture was heated to 35° C. to dissolve any product that may have precipitated, then transferred to a sintered glass pressure filter containing 3 grams of filter aid while still warm. The filtration was complete in two minutes with three psi argon pressure. The equipment and muds were rinsed with 2×40 ml of warm cyclohexane. This afforded 320.9 grams of slightly hazy, pale yellow solution. Titration of the active C—Li indicated 0.316 M (0.4063 moles/kg) which represented a 77.8% yield.

The foregoing examples are illustrative of the present invention and are not to be construed as limiting thereof.

That which is claimed is:

1. A process for preparing haloamine electrophiles, comprising reacting one or more amines with at least one $\alpha,\omega$-dihaloalkane or $\alpha,\omega$-dihaloalkene or a mixture thereof, said $\alpha,\omega$-dihaloalkane or $\alpha,\omega$-dihaloalkene having two displaceable halides, in the absence of a phase transfer catalyst, wherein said reacting step is not initiated by ultraviolet radiation.

2. The process of claim 1, wherein said reacting step takes place in the presence of an acid acceptor.

3. The process of claim 1, wherein said reacting step takes place in a solvent.

4. The process of claim 1, wherein said one or more amines is selected from the group consisting of t-butyl amine, hexamethyleneimine, 1-methyl-1,4-diazacycloheptane (1-methylhomopiperazine), piperidine, pyrrolidine, ethyl amine, dimethyl amine, morpholine, 1-methyl piperazine, and mixtures thereof.

5. The process of claim 1, wherein said at least one α,ω-dihaloalkane or α,ω-dihaloalkene or mixture thereof is selected from the group consisting of 1-bromo-3-chloropropane, 1-bromo-4-chloro-butane, 1-bromo-5-chloropentane, 1-bromo-6-chloro-hexane, 1-bromo-8-chlorooctane, 1,4-dichloro-2-butene, 1,3-dibromopropane, 1,3-dichloropropane, 1,4-dibromobutane, 1,4-dichlorobutane, 1-bromo-3-chloro-2-methylpropane, 1,3-dibromo-2-methylpropane, 1,3-dichloro-2-methylpropane, 1,3-dichloro-2,2-dimethylpropane, 1,3-dibromo-2,2-dimethylpropane, 1-bromo-3-chloro-2,2-methylpropane, and mixtures thereof.

6. The process of claim 1, wherein said amine is hexamethyleneimine and said at least one α,ω-dihaloalkane or α,ω-dihaloalkene is 1-bromo-3-chloropropane.

7. The process of claim 1, wherein said amine is 1-methylhomopiperizine and said at least one α,ω-dihaloalkane or α,ω-dihaloalkene is 1-bromo-3-chloropropane.

8. The process of claim 1, wherein said amine is hexamethyleneimine and said at least one α,ω-dihaloalkane or α,ω-dihaloalkene is 1,4-dichloro-2-butene.

9. The process of claim 2, wherein said acid acceptor is selected from the group consisting of potassium carbonate, sodium bicarbonate, triethylamine, pyridine, trimethylamine, and mixtures thereof.

10. The process of claim 3, wherein said solvent is selected from the group consisting of water, tetrahydrofuran, hexane, cyclohexane, toluene, acetonitrile, methyl-t-butyl ether, diethoxymethane, methanol, and mixtures thereof.

11. A process for preparing haloamine electrophiles, comprising reacting hexamethyleneimine with at least one α,ω-dihaloalkane or α,ω-dihaloalkene or a mixture thereof, said α,ω-dihaloalkane or α,ω-dihaloalkene having two displaceable halides in the absence of a phase transfer catalyst, wherein said reacting step is not initiated by ultraviolet radiation.

12. The process of claim 11, wherein said α,ω-dihaloalkane or α,ω-dihaloalkene is 1,4-dichloro-2-butene.

13. The process of claim 11, wherein said α,ω-dihaloalkane or α,ω-dihaloalkene is 1-bromo-3-chloropropane.

14. The process of claim 1, wherein said α,ω-dihaloalkane or α,ω-dihaloalkene or mixture thereof comprises halogen atoms selected from the group consisting of bromine, chlorine and mixture thereof.

15. The process of claim 1, wherein said reacting step takes place in the presence of less than or about 1 equivalent solvent.

16. The process of claim 1, wherein said reacting step takes place without solvent.

17. The process of claim 11, wherein said α,ω-dihaloalkane or α,ω-dihaloalkene or mixture thereof comprises halogen atoms selected from the group consisting of bromine, chlorine and mixture thereof.

18. The process of claim 11, wherein said reacting step takes place in the presence of less than or about 1 equivalent solvent.

19. The process of claim 11, wherein said reacting step takes place without solvent.

* * * * *

UNITED STATES PATENT AND TRADEMARK OFFICE
CERTIFICATE OF CORRECTION

PATENT NO.   : 6,717,014 B1  
DATED        : April 6, 2004  
INVENTOR(S)  : Schwindeman et al.

It is certified that error appears in the above-identified patent and that said Letters Patent is hereby corrected as shown below:

Title page,
Item [56], References Cited, OTHER PUBLICATIONS, include the following references:

-- Stephenson E. (Org. Synthesis, Coll. Vol. 111, pages 475-483, 1955).
Reisinger, Kurt (CA 90:54458 abstract of DE 27 19365)
Hayase et al. (CA 111: 153338 abstract of JP63227552)
Erra-Balsels et al. (CA 111:39159 abstract of An. Asoc. Quim. Argent. (1988), 76(4), 285-96)
Turks et al. (J. Med. Chem. Vol. 9, (1966), pages 191-195) --

Column 10,
Line 45, should read -- was added. The reaction mixture was stirred at 45-50º C. for --

Signed and Sealed this

Twenty-first Day of September, 2004

JON W. DUDAS  
*Director of the United States Patent and Trademark Office*